(12) United States Patent
Silberberg et al.

(10) Patent No.: US 7,498,565 B2
(45) Date of Patent: Mar. 3, 2009

(54) METHOD OF AND SYSTEM FOR SELECTIVE CELL DESTRUCTION

(75) Inventors: Yaron Silberberg, LeHavim (IL); Dvir Yelin, Jerusalem (IL); Dan Oron, Rechovot (IL)

(73) Assignee: Yeda Research and Development Co. Ltd., Rechovot (IL)

( * ) Notice: Subject to any disclaimer, the term of this patent is extended or adjusted under 35 U.S.C. 154(b) by 402 days.

(21) Appl. No.: 10/562,001

(22) PCT Filed: Jun. 9, 2004

(86) PCT No.: PCT/IL2004/000491

§ 371 (c)(1),
(2), (4) Date: May 1, 2006

(87) PCT Pub. No.: WO2004/112882

PCT Pub. Date: Dec. 29, 2004

(65) Prior Publication Data

US 2006/0241585 A1 Oct. 26, 2006

(30) Foreign Application Priority Data

Jun. 24, 2003 (IL) .................................. 156626

(51) Int. Cl.
*A61B 18/00* (2006.01)
*A61B 18/18* (2006.01)
(52) U.S. Cl. .............................. 250/251; 606/1; 606/2; 606/10; 606/11; 606/12; 606/13; 606/14
(58) Field of Classification Search .................. 250/251
See application file for complete search history.

(56) References Cited

U.S. PATENT DOCUMENTS

| 5,980,512 | A | 11/1999 | Silberg |
| 6,104,426 | A | 8/2000 | Street |
| 6,620,154 | B1 | 9/2003 | Amirkhanian et al. |
| 6,780,184 | B2 | 8/2004 | Tanrisever |

FOREIGN PATENT DOCUMENTS

| WO | WO 01/06257 | 1/2001 |
| WO | WO 02/28552 | 4/2002 |

OTHER PUBLICATIONS

Zhang et al. "Application of the Biological Conjugate Between Antibody and Colloid Au Nanoparticles as Analyte to Inductively Coupled Plasma Mass Spectrometry", Analytical Chemistry, 74(1): 96-99, 2002.
Ni et al. "Immunoassay Readout Method Using Extrinsic Raman Labels Adsorbed on Immunogold Colloids", Analytical Chemistry, 71(21): 4903-4908, 1999.
Lyon et al. "Colloidal Au-Enhanced Surface Plasmon Resonance Immunosensing", Analytical Chemistry, 70(24): 5177-5183, 1998.
Quinten "Local Fields Close to the Surface of Nanoparticles and Aggregates of Nanoparticles", Applied Physics B, Lasers and Optic, 73: 245-255, 2001.
Averitt et al. "Linear Optical Properties of Gold Nanoshells", Journal of the Optical Society of America, 16(10): 1824-1832, 1999.
Doremus et al. "Optical Properties of Nanosized Gold Particles", Journal of Materials Research, 11(11): 2834-2840, 1996.

*Primary Examiner*—David A. Vanore

(57) ABSTRACT

Method and apparatus for the ionization of living cells where an optical device (14) delivers an optical pulse having an optical field power which is modified locally by an optical field power modifying means (18) to effect ionization and destruction of living cells (16).

22 Claims, 2 Drawing Sheets

METHOD OF AND SYSTEM FOR SELECTIVE CELL DESTRUCTION

RELATED APPLICATIONS

This application is a National Phase Application of PCT Application No. PCT/IL2004/000491 having International Filing Date of Jun. 9, 2004, which claims the benefit of Israel Patent Application No. 156626, filed on Jun. 24, 2003. The contents of the above Applications are all incorporated herein by reference.

FIELD AND BACKGROUND OF THE INVENTION

The present invention relates to a method and system for destruction of biological tissues and/or cells via selective ionization and, more particularly, to a method of ionizing biological tissues and/or cells using metallic nano-particles and electromagnetic irradiation.

Cancer is a major cause of death in the modern world. Effective treatment of cancer is most readily accomplished following early detection of malignant tumors. Most techniques used to treat cancer (other than chemotherapy) are directed against a defined tumor site in an organ, such as brain, breast, ovary and colon tumors, etc. When a mass of abnormal cells is consolidated and is sufficiently large, either surgical removal, destruction of the tumor mass using either heating, cooling, radiative or chemical ablation becomes possible because the target is readily identifiable and localizable. However, it is not uncommon for a cancer that has initially occurred at a primary site to metastasize and spread into adjacent organs as diffuse clusters of abnormal cells. These small clusters of cells, which are more properly referred to as microscopic diffuse metastatic deposits, are not localizable and are virtually impossible to treat other than by systemic chemotherapy or radiotherapy. Yet, because of the diverse nature of cancer cells, only a portion of the metastatic abnormal cells will likely be susceptible to chemotherapy or radiotherapy, leaving abnormal cells that are resistant to the therapy to multiply until the patient dies from the concomitant effects of the malignant cells.

Recently, light and more specifically laser light has been used for non-invasive detection as well as destruction of malignant cells. Laser technology has found many applications in medicine and biology including destruction of cells or tissues, e.g., for the purpose of cancer treatment. Destruction of unwanted cells can be achieved either through a direct interaction between the laser beam and the tissue, or through activation of some photochemical reactions using light-activated molecules which are injected into or otherwise administered to the tissue.

Photo-dynamic therapy (PDT) is a relatively new approach for treating many cancers. At the first step of treatment, one or more drugs that bind to rapidly dividing cells are administered either directly to a tissue or organ or systemically to the treated subject. The drugs administered for PDT are commonly known as photosensitizers due to their inherent ability to absorb photons of light and transfer that energy to oxygen which then converts to a cytotoxic or cytostatic species. Approximately 24-48 hours after the injection, a narrow-band laser is used to excite the photosensitive drug, inducing a chemical reaction which results in a production of free radicals and/or other reactive products that destroy the abnormal tissue or cell with relatively small damage to the surrounding healthy tissue.

To date, PDT has been used to treat esophageal cancer, early stage lung cancer, Kaposi's sarcoma, an AIDS related condition, atherosclerotic plaques, lesions of surface skin diseases, overgrowth of blood vessels in the eye (macular degeneration) and unwanted pathogens in the blood.

The effectiveness of the PDT process depends on the amount of photosensitizer at the target, the absorption properties of the environment neighboring the target and photosensitizer, and a number of physiologic factors such as temperature, pH, oxygen content, and the sensitivity of the target to the photosensitizer generated reaction.

Known PDT techniques suffer from a number of drawbacks and limitations. It is necessary to deliver a large amount of light radiation to the tumor at specific wavelengths to activate the photosensitive agent. Most photosensitive agents are activated at wavelengths that can only penetrate through three or less centimeters of tissue. Hence, non- or minimal-invasive PDT can be used for cancerous growths that are on or near the surface of the skin, or on the lining of internal organs.

Typical prior art PDT light delivery systems have used monochromatic lasers in combination with fiber optic catheters, for example by providing a monochromatic light to a fiber optic bundle, which in turn transmits the light through a light diffuser to the tumor. One disadvantage of such PDT delivery system is that a typical fiber optic catheter transmits only about 30% to 50% of available light energy. Additional energy losses occur in the diffuser which surrounds the light-emitting end of the catheter and diffuses the light emanating from the catheter. The blood and the surrounding tissue also attenuate a substantial portion of the input power. The net result is that only about 25% to 30% of the power is available to activate the photosensitive agent. Besides increasing the required size and cost of the light source, these energy losses also reduce the effectiveness of the treatment since the depth of radiation penetration into the tissue is reduced. With reduced penetration, surgical techniques are required to remove much of the malignant tissue before photodynamic therapy commences, and the likelihood that all malignant tissue is destroyed is lessened.

Another drawback of PDT techniques is that the photosensitizing drug remains in the bloodstream for six weeks or more, causing patients to be extremely light sensitive during that time period.

The present invention provides solutions to the problems associated with prior art cell destruction techniques.

SUMMARY OF THE INVENTION

According to one aspect of the present invention there is provided a method of destroying living cells, the cells being characterized by an ionization threshold, the method comprising: providing at least one optical pulse having an optical field power smaller than the ionization threshold of the cells; and generating conditions for locally increasing the optical field power per unit area beyond the ionization threshold of the cells, thereby destroying the cells via ionization.

According to further features in preferred embodiments of the invention described below, the generating conditions for locally increasing the optical field power per unit area is by a plurality of particles, at least a portion of each of the plurality of particles is made of a conducting material.

According to another aspect of the present invention there is provided a method of destroying living cells, the cells being characterized by an ionization threshold, the method comprising: administrating a plurality of particles to the cells, at least a portion of each of the plurality of particles is made of a conducting material; and directing at least one optical pulse toward at least a portion of the cells; the particles and the at least one optical pulse are selected and designed so as to provide a local enhancement of an optical field to a power per unit area which is beyond the ionization threshold of the cells, thereby destroying the cells via ionization.

According to further features in preferred embodiments of the invention described below, the method further comprising focusing a beam of the at least one optical pulse, so as to increase the optical field power per unit area.

According to still further features in the described preferred embodiments the focusing is done by a converging lens.

According to yet another aspect of the present invention there is provided a system for destroying living cells, the cells being characterized by an ionization threshold, the system comprising: an optical device for providing at least one optical pulse having an optical field power which is smaller than the ionization threshold of the cells; and a mechanism for locally increasing the optical field power per unit area beyond the ionization threshold of the cells, thereby destroying the cells via ionization.

According to further features in preferred embodiments of the invention described below, the mechanism for locally increasing the optical field power per unit area comprises a plurality of particles, at least a portion of each of the plurality of particles is made of a conducting material.

According to still further features in the described preferred embodiments the system further comprising at least one optical element for focusing a beam of the at least one optical pulse, so as to increase the optical field power per unit area.

According to still another aspect of the present invention there is provided an ablative procedure for destroying living cells present in a body of a subject, the cells being characterized by an ionization threshold, the ablative procedure comprising: administrating a plurality of particles to the body of the subject, at least a portion of each of the plurality of particles is made of a conducting material; directing at least one optical pulse toward at least a portion of the cells; the particles and the optical pulses are selected and designed so as to provide a local enhancement of an optical field to a power per unit area which is beyond the ionization threshold of the cells, thereby destroying the cells via ionization.

According to further features in preferred embodiments of the invention described below, the directing at least one optical pulse is by inserting a light transmitting device into the body of the subject; and using the light transmitting device for According to still further features in the described preferred embodiments inserting the light transmitting device into the body is by endoscopy.

According to still further features in the described preferred embodiments inserting the light transmitting device into the body is by laparoscopy.

According to an additional aspect of the present invention there is provided a light transmitting device for destroying living cells present in a body of a subject, the device comprising: an optical device for emitting a at least one optical pulse having a duration in a femtosecond time scale; and a waveguide for guiding the optical pulses into a body of a subject; the waveguide having an emission face, through which the optical pulses are emitted to the living cells, thereby destroying the cells via ionization.

According to further features in preferred embodiments of the invention described below, the waveguide comprise a fiber optic bundle.

According to still further features in the described preferred embodiments the waveguide is sterile.

According to still further features in the described preferred embodiments the waveguide is covered by a disposable sterile coat.

According to still further features in the described preferred embodiments the cells form a part of an organ.

According to still further features in the described preferred embodiments the cells form a part of a tumor.

According to still further features in the described preferred embodiments the cells form a part of a malignant tumor.

According to still further features in the described preferred embodiments the cells form a part of a blood vessel.

According to still further features in the described preferred embodiments the cells form a part of a pathological tissue.

According to still further features in the described preferred embodiments the cells form a part of a restenotic tissue.

According to still further features in the described preferred embodiments the ionization threshold is from about $10^{10}$ Watts/cm$^2$ to about $10^{14}$ Watts/cm$^2$.

According to still further features in the described preferred embodiments the light transmitting device comprises a fiber optic bundle.

According to still further features in the described preferred embodiments a duration of the at least one optical pulse is selected so as to avoid heating of the cells by linear absorption.

According to still further features in the described preferred embodiments the duration is in a femtoseconds time scale.

According to still further features in the described preferred embodiments a wavelength of the at least one optical pulse is from about 400 nm to about 1300 nm.

According to still further features in the described preferred embodiments a repetition-rate of the at least one optical pulses is from a 10 pulses/second to about $10^{10}$ pulses/second.

According to still further features in the described preferred embodiments the pulses having a high peak-power.

According to still further features in the described preferred embodiments the pulses having a low average-intensity.

According to still further features in the described preferred embodiments the peak-power is below the ionization threshold of the living cells.

According to still further features in the described preferred embodiments the average-intensity is below a heating damage threshold of the living cells.

According to still further features in the described preferred embodiments the average-intensity is lower than 1 Watt/cm$^2$.

According to still further features in the described preferred embodiments the light transmitting device comprises at least one optical element for focusing a beam of said at least one optical pulse, so as to increase said optical field power per unit area.

According to still further features in the described preferred embodiments the at least one optical element is a converging lens.

According to still further features in the described preferred embodiments each of the plurality of particles comprises an affinity component having affinity to the living cells.

According to still further features in the described preferred embodiments a size of each of the plurality of particles is from 1 nm to 200 nm.

According to still further features in the described preferred embodiments the particles are biocompatible.

According to still further features in the described preferred embodiments the particles are metallic particles.

According to still further features in the described preferred embodiments the conducting material is comprised of at least one metal selected from the group consisting of coinage metals, noble metals, transition metals and synthetic metals.

According to still further features in the described preferred embodiments the synthetic metals are selected from the group consisting of polyacetylene and polyanaline.

According to still further features in the described preferred embodiments the conducting material is gold.

According to still further features in the described preferred embodiments the conducting material comprises a metal-like material.

According to still further features in the described preferred embodiments the conducting material comprises a metal alloy.

According to still further features in the described preferred embodiments the affinity component comprises a moiety selected from the group consisting of an antibody, an antigen, a ligand and a substrate.

According to still further features in the described preferred embodiments the moiety is selected so as to ensure attachment of the particles to a predetermined part of the cell, which is selected from the group consisting of nucleus, nucleolus, mitochondria, membrane, DNA, RNA, proteins, endoplasmic reticulum and Golgi apparatus.

According to still further features in the described preferred embodiments the particles comprise a conducting shell layer characterized by a shell-thickness, having a first radius and a second radius.

According to still further features in the described preferred embodiments a ratio between the first radius and the second radius is selected so as to obtain a predetermined plasmon-resonance frequency of the particles.

According to still further features in the described preferred embodiments the predetermined resonance frequency is a near infrared resonance frequency.

According to still further features in the described preferred embodiments the thickness is from 1 nm to 100 nm.

According to still further features in the described preferred embodiments the conducting shell layer immediately adjacent to and independently layered upon a non-conducting core layer.

According to still further features in the described preferred embodiments the non-conducting core layer comprises a dielectric material.

According to still further features in the described preferred embodiments the dielectric material is selected from the group consisting of silicon dioxide, titanium dioxide, PMMA, polystyrene, and dendrimers.

According to still further features in the described preferred embodiments the non-conducting core layer comprises a semi-conducting material.

According to still further features in the described preferred embodiments the non-conducting core layer comprises at least one molecule selected from the group consisting of an organic molecule and an organic super-molecular structure.

According to still further features in the described preferred embodiments the non-conducting core layer comprises a mixture of non-conducting materials.

According to still further features in the described preferred embodiments the non-conducting core layer comprises an optically absorbing material.

According to still further features in the described preferred embodiments the non-conducting core layer comprises a fluorescent material.

According to still further features in the described preferred embodiments the optical device has a peak-power from about $10^5$ Watts to about $10^{10}$ Watts.

The present invention successfully addresses the shortcomings of the presently known configurations by providing a method and system for destroying living cells far exceeding prior art.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
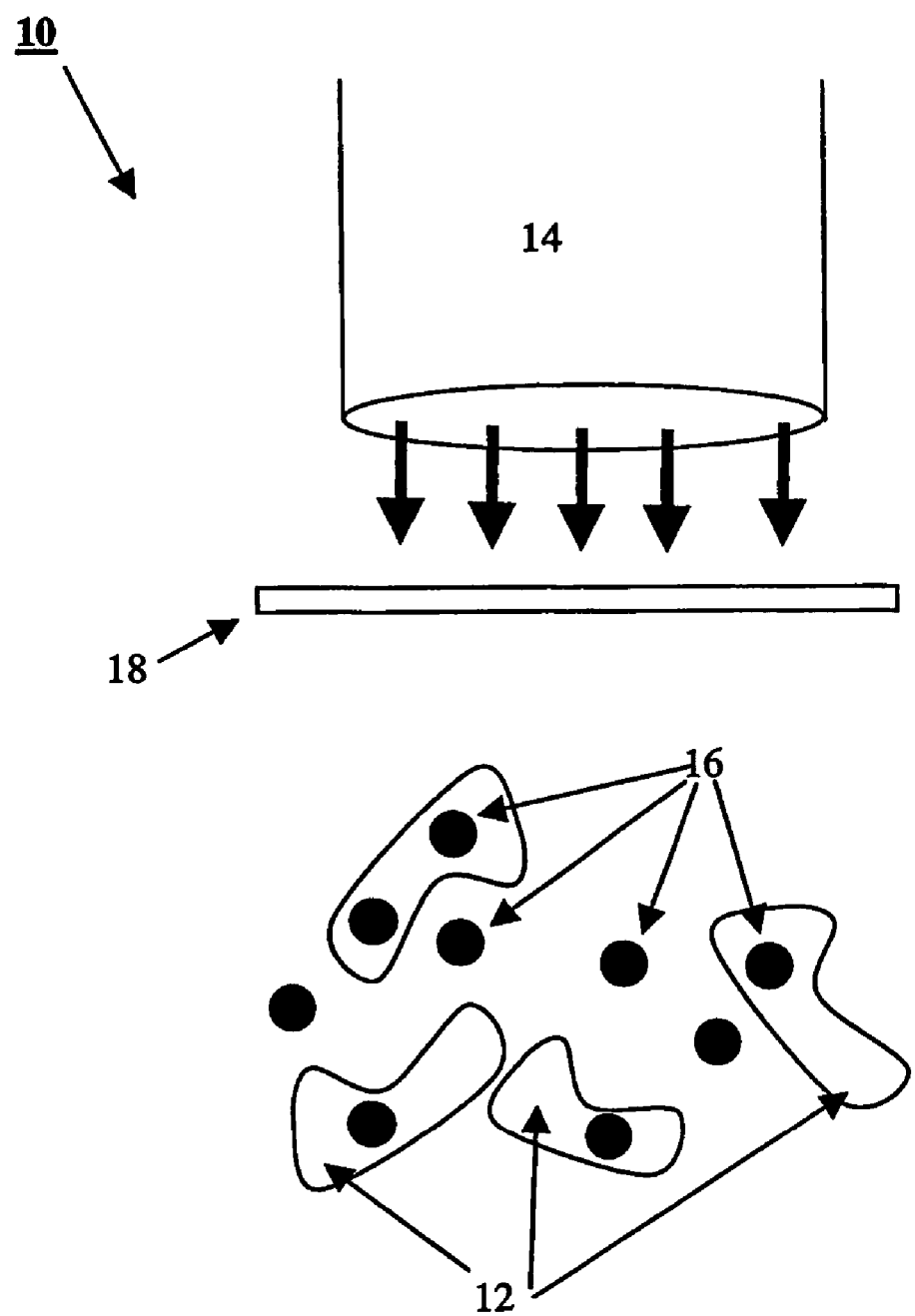
FIG. 1 is a system for destroying living cells, according to the present invention.

The present invention is of a method and a system for destroying living cells by ionization, which can be used for tissue/cell ablation. Specifically, the present invention can be used to remove clusters of cells either by invasive or non-invasive medical procedures.

The principles and operation of a method and a system for destroying living cells according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a system 10 for destruction of living cells 12. According to the present invention, cells 12 are characterized by an ionization threshold, measurable in units of energy per time unit per area unit, e.g., Watts/cm². Cells 12 may form any part of the human body, for example, an organ or a part of an organ, e.g., a blood vessel or part thereof, a tumor (malignant or benign) and any other pathological tissue, e.g., a restenotic tissue. A typical ionization threshold for cells 12 is, in terms of orders of magnitude, from $10^{10}$ Watts/cm² to $10^{14}$ Watts/cm².

According to a preferred embodiment of the present invention system 10 includes an optical device 14 for providing an optical field power smaller than the ionization threshold and a mechanism 16 for locally increasing the optical field power per unit area beyond the ionization threshold of the cells. The optical filed, as provided by optical device 14 is in a form of at least one light pulse (e.g., a sequence of laser pulses), the duration and the repetition-rate of which are chosen so as to avoid heating of the cells by linear absorption. A typical pulse duration is in a femtoseconds time scale, e.g., about $10\text{-}1000 \cdot 10^{-15}$ seconds.

As used herein, the term about refers to $\pm 10\%$.

Optical device 14 provides a laser beam having a high peak-power with a low average-intensity. According to a preferred embodiment of the present invention, the peak-power of the laser is below the ionization threshold and the average-intensity is below the heating damage threshold for bodily tissues.

The desired peak and average intensities may be achieved in more than one way. Hence, in one embodiment of the present invention, device 14 may be provided as an amplified, low repetition-rate femtosecond laser system having a peak-power of about $10^{10}$ Watts. In another embodiment of the present invention, device 14 may be a high repetition-rate femtosecond laser system having a peak power of about $10^5$ Watts. It is to be understood that in the latter embodiment the illuminated area should be sufficiently small and the beam should be focused by at least one optical element 18 to achieve high optical field power per unit area at the cell. Optical element 18 may be any known element for focusing (e.g. collimating) an optical beam, such as, but not limited to a converging lens.

Typical repetition rates are from about 10 pulses/second for a low repetition-rate laser system to about $10^{10}$ pulses/second for a high repetition-rate femtosecond laser system. One ordinarily skilled in the art would appreciate that a penetration depth of the laser beam into the body depends on the wavelength of the optical field. It is known that human tissues are relatively transparent to light in the near-infrared region (NIR) of the spectrum. When deep penetration is desired, a preferred wavelength of the laser beam is from about 800 nm to about 1300 nm, however, shorter wavelengths (e.g. 400 nm to 800 nm) may also be used, for abnormal cells growths that are on or near the surface of the skin, or on the lining of internal organs.

Unlike prior art teachings, where the power of the laser beam is above the ionization threshold, optical device 14 provides a pulse power which is below ionization threshold hence there is no global cell destruction across the entire illumination area, along its efficient penetration depth.

Mechanism 16 serves, according to the gist of the present invention, for increasing the laser field beyond the ionization threshold only within a limited volume where unwanted cells are present. Thus, system 10 has the advantage of selectively destroying unwanted cells by ionization, while leaving other neighboring cells substantially undamaged.

According to a preferred embodiment of the present invention mechanism 16 may be any mechanism capable of locally increasing the optical field. Thus, for example, mechanism 16 may include a plurality of particles, at least a portion of each of the particles is made of a conducting material. Hence, the particles may be, for example, metallic particles.

Each of the particles may also include an affinity component, whereby the affinity component has affinity to the living cells to be destroyed. The particles have a diameter which is preferably from 1 nm to 200 nm, so as to allow a substantial increment of the nearby optical field, which increment is larger for smaller particles. The affinity component of the particles ensures a short distance between the particles and the unwanted cells, hence when the optical field is increased near the particles, a selective destruction of the cells occurs. When ionization occurs at a living cell, it is destroyed irrespectively to the location at which the ionization is initiated. Thus, the affinity of the particles may be selected so that the particles will attach to any part of the cell, e.g., nucleus, nucleolus, mitochondria, membrane, DNA, RNA, proteins and the like.

As used herein, the term nanoparticle refers to a particle or particles of nano-meter size range, e.g., $1\text{-}200 \cdot 10^{-9}$ m.

The physical process of strong field enhancement very close to metal nanoparticles is a well known phenomenon and has been described in detail in the literature. To this end, see, for example, R. H. Doremus and P. Rao, *J. Mater. Res.*, 11, 2834 (1996); M. Quinten, *Appl. Phys.* B 73, 245 (2001) and R. D. Averitt, S. L. Westcott and N. J. Halas, *J. Opt. Soc. Am.* B 16, 1824 (1999), the contents of which are hereby incorporated by reference.

In metal nanoparticles, resonant collective oscillations of conduction electrons, also known as particle plasmons, are excited by an optical field. The resonance frequency of a particle plasmon is determined mainly by the dielectric function of the metal, the surrounding medium and by the shape of the particle. Resonance leads to a narrow spectrally selective absorption and an enhancement of the local field confined on and close to the surface of the metal particle. The spectral width of absorption and near-field enhancement depends on the decay time of the particle plasmons.

When the laser wavelength is tuned to the plasmon resonance frequency of the particle, the local electric field in proximity to the nano-particles could be enhanced by several orders of magnitude.

Figure 2:
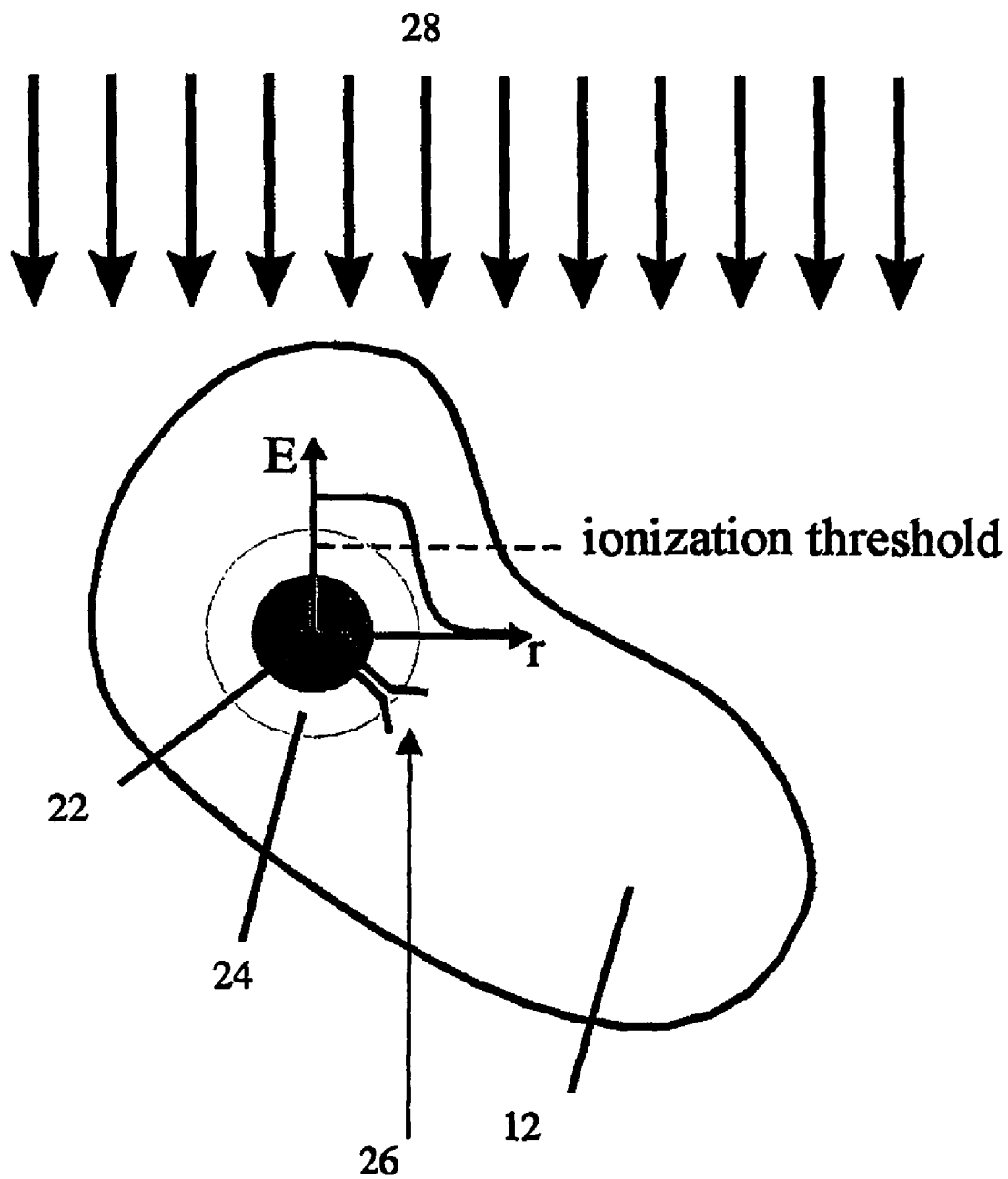
FIG. 2 is a nanoparticle captured in a cell, according to the present invention.

Reference is now made to FIG. 2, which illustrates a nanoparticle 22 which is captured by one of living cells 12. Nanoparticle 22 includes affinity component 26, which specifically attaches nanoparticle 22 to cell 12. Cell 12 and nanoparticle 22 are illuminated by laser beam 28. The optical field of beam 28 is increased in a volume 24 neighboring nanoparticle 22.

When the optical field interacts with atoms or molecules present in volume 24, the electrons are oscillating due to the force exerts by the field oscillations. When the field power per unit area reaches above the ionization threshold, the electrons detach from the atoms. The free electrons that are formed after the initial ionization are accelerated by the optical field and interact with other molecules, leading to the creation of local damage. Because the pulse power of laser beam 28 is below the ionization threshold of cells 12, the damage is constrained only to volume 24.

The structure size and shape of the nanoparticles are designed in accordance with the specific application for which system 10 is used. Specifically, the size of the nanoparticles is selected so that the resonance frequency of the nanoparticles and the frequency of the optical pulses substantially coincide. Hence, in preferred embodiments in which the pulses are of short wavelengths (e.g., 400-800 nm for near-skin treatments), the nanoparticles are about 1-50 nm in diameter. Longer wavelengths (e.g., near infrared), which allow deep penetration depth of the optical pulses into the body, require larger nanoparticles, about 100-200 nm in diameter.

It is often desired to further minimize the nanoparticles size, for example, to enhance the effect of optical field increment or to allow the nanoparticles to penetrate into the cells. This may be done, by providing nanoparticles which include a dielectric core and a conducting shall layer. Nanoparticles having such structure are called nanoshells. Although nanoshells are especially useful in cases of near infrared wavelengths applications, they may also be used for short wavelengths applications.

The process of manufacturing nanoshells having a dielectric core and a conducting shell, is known in the art and is described in, for example, WO 01/06257 and WO 02/28552, the contents of which are hereby incorporated by reference.

For any given core and shell materials, the ratio between the core radius and the total radius of nanoshells can be chosen for maximum scattering and minimum absorption at a specific resonance frequency. Based on the core to total radii ratios, the nanoshells manifesting plasmon resonances extending from ultraviolet to infrared can be readily fabricated. Hence, the core diameters of the nanoshells may range from about 1 nm to about 400 nm or more, and the shell thickness may range from about 1 nm to about 100 nm. For a near infrared light, the total diameter of the nanoshells may be reduced down to 20 nm.

According to a preferred embodiment of the present invention the non-conducting core layer may be, for example, a semi-conducting material, an organic molecule, an organic super-molecular structure, or any mixture of non-conducting materials. Optionally, the non-conducting core layer may include an optically absorbing material, and/or a fluorescent material.

According to another aspect of the invention there is provided a method of destroying living cells, characterized by an ionization threshold. The method comprises the following steps which may be executed using an appropriate system, device or apparatus, e.g., system 10, as described hereinabove. Hence, at least one optical light pulse is provided, having an optical field power smaller than the ionization threshold of the cells, while generating conditions for locally increasing the optical field power per unit area beyond the ionization threshold of the cells. Hence the cells are destroyed via ionization. The conditions for locally increasing the optical field may be generated, for example, by administrating particles such as, e.g., nanoparticles 22 to the cells, as is further detailed hereinabove.

According to an additional aspect of the invention there is provided a light transmitting device for destroying living cells present in a body of a subject. The device may be used, e.g., by system 10, as optical device 14 (FIG. 1). According to a preferred embodiment of the present invention the device includes an optical device for emitting at least one optical pulse having a duration which is preferably in a femtosecond time scale. The device further includes a waveguide, e.g., fiber optic bundle, for guiding the optical pulses into a body of a subject. The waveguide having an emission face, through which the optical pulses are emitted to the living cells, hence the cells are destroyed as detailed above. The device may be used either in an invasive medical procedure or in non-invasive medical procedure. In any case, the waveguide is preferably sterile. The sterilization of the waveguide may be, for example by a disposable sterile coat, which covers at least a portion of the waveguide.

The present invention successfully provides an ablative procedure for destroying living cells present in a body of a subject. The ablative procedure includes the following steps, which may be executed, for example, using system 10. In a first step of the procedure a plurality of particles are administrated to the body of the subject. The particles are similar to the nanoparticles described hereinabove. In a second step, at least one optical pulse is directed toward at least a portion of the cells.

According to a preferred embodiment of the present invention the second step may be done by a light transmitting device which may inserted into the body of the subject. The light transmitting device may be any device known in the art for transmitting, e.g., a laser beam, e.g., a fiber optic bundle. In a third step of the procedure the light transmitting device is used for.

Similarly to the above embodiments, the particles and the pulse (or pulses) are selected and designed so as to provide a local enhancement of an optical field to a power per unit area which is beyond the ionization threshold of the cells, thereby destroying the cells via ionization.

According to a preferred embodiment of the present invention the light transmitting device is inserted into the body by either endoscopy or laparoscopy. In addition, the ablation procedure may be executed in parallel to another surgical procedure, while the unwanted cells of the subject are exposed.

Suitable metals for forming the metallic nanoparticles or the outer layer of the nanoshells include the noble and coinage metals, but other electrically conductive metals may also be employed. Metals that are particularly well suited for use in shells include but are not limited to gold, silver, copper, platinum, palladium, lead, iron or the like. Gold and silver are preferred. Alloys or non-homogenous mixtures of such metals may also be used.

Gold nanoparticles are suitable markers in biotechnological systems because specific activities of micro-molecules can be retained when coupling micro-molecules to gold nanoparticles. In addition, gold nanoparticles can be easily visualized by electron microscopy. Since gold is inert, gold nanoparticles are highly biocompatible.

Suitable dielectric core materials of the nanoshells used in the present invention include, but are not limited to, silicon dioxide, goldsulfide, titanium dioxide, polymethyl methacrylate (PMMA), polystyrene, and macromolecules such as dendrimers. The core of the nanoparticle may also be a combination or a layered combination of dielectric materials such as those listed above.

According to a preferred embodiment of the present invention the living cells may form a part of a tumor. Typical tumors include, but are not limited to, breast tumor, brain tumor, neuroblastoma, thyroid gland tumor, gestational trophoblastic tumor, uterine sarcoma, carcinoid tumor, colon carcinoma, esophageal carcinoma, hepatocellular carcinoma, liver carcinoma, lymphoma, plasma cell neoplasm, mesothelioma, thymoma, alveolar soft-part sarcoma, angiosarcoma, epithelioid sarcoma, extraskeletal chondrosarcoma, fibrosarcoma, leiomyosarcoma, liposarcoma, malignant fibrous histiocytoma, malignant hemangiopericytoma, malignant mesenchymoma, malignant schwannoma, synovial sarcoma, melanoma, neuroepithelioma, osteosarcoma, leiomyosarcoma, Ewing sarcoma, osteosarcoma, rhabdomyo-sarcoma, hemangiocytoma, myxosarcoma, mesothelioma (e.g., lung mesothelioma), granulosa cell tumor, the coma cell tumor and Sertoli-Leydig tumor.

Hence, the present invention can be used to treat many types of cancers, such as, but not limited to, vaginal cancer, vulvar cancer, cervical cancer, endometrial cancer, ovarian cancer, rectal cancer, salivary gland cancer, laryngeal cancer, nasopharyngeal cancer, many lung metastases and acute or chronic leukemia (e.g., lymphocytic, Myeloid, hairy cell).

According to a preferred embodiment of the present invention, the affinity component of the nanoparticles includes a moiety which may be, for example an antibody, an antigen, a ligand or a substrate. The techniques of attaching proteins and other chemicals, to the surfaces of metal nanoparticles, are well known in the art. To this end, see, e.g., C. Zhang et. al., *Anal. Chem.* 74, 96 (2002); J. Ni et. al. *Anal. Chem.* 71, 4903 (1999); L. Lyon, et. al., *Anal. Chem.* 70, 5177 (1998), the contents of which are hereby incorporated by reference.

The following lists some primary antibodies known to specifically bind their associated cytological markers and which are presently employed as affinity components in immunohistochemical stains used for research and, in limited cases, for diagnosis and therapy of various diseases. Anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oncoprotein (p21) antibody, anti-Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (Alzheimer's disease), anti-fibrin antibody (epithelial cells), anti-keratins antibody, and anti-Tn-antigen antibody (colon carcinoma, adenocarcinomas, and pancreatic cancer).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of destroying living cells, the cells being characterized by an ionization threshold, the method comprising:
   providing at least one optical pulse having an optical field power smaller than the ionization threshold of the cells while generating conditions for locally increasing said optical field power per unit area beyond the ionization threshold of the cells, thereby destroying the cells via ionization.

2. The method of claim 1, wherein the cells form a part of a pathological tissue.

3. The method of claim 1, wherein a duration of said at least one optical pulse is selected so as to avoid heating of the cells by linear absorption.

4. The method of claim 3, wherein said duration is in a femtoseconds time scale.

5. The method of claim 1, wherein a wavelength of said at least one optical pulse is from about 400 nm to about 1300 nm.

6. The method of claim 1, wherein said generating conditions for locally increasing said optical field power per unit area is by a plurality of particles, at least a portion of each of said plurality of particles is made of a conducting material.

7. A method of destroying living cells, the cells being characterized by an ionization threshold, the method comprising:
   administrating a plurality of particles to the cells, each of said plurality of particles, at least a portion of each of said plurality of particles is made of a conducting material; and
   directing at least one optical pulse toward at least a portion of the cells;
   said particles and said at least one optical pulse are selected and designed so as to provide a local enhancement of an optical field to a power per unit area which is beyond the ionization threshold of the cells, thereby destroying the cells via ionization.

8. The method of claim 7, wherein each of said plurality of particles comprises an affinity component having affinity to the living cells.

9. The method of claim 7, wherein the cells form a part of a pathological tissue.

10. The method of claim 7, wherein a duration of said at least one optical pulse is selected so as to avoid heating of the cells by linear absorption.

11. The method of claim 7, wherein a wavelength of said at least one optical pulse is from about 400 nm to about 1300 nm.

12. A system for destroying living cells, the cells being characterized by an ionization threshold, the system comprising:
   an optical device for providing at least one optical pulse having an optical field power which is smaller than the ionization threshold of the cells; and a mechanism for locally increasing said optical field power per unit area beyond the ionization threshold of the cells, thereby destroying the cells via ionization.

13. The system of claim 12, wherein said mechanism for locally increasing said optical field power per unit area comprises a plurality of particles, at least a portion of each of said plurality of particles is made of a conducting material.

14. The system of claim 13, wherein each of said plurality of particles comprises an affinity component having affinity to the living cells.

15. The system of claim 13, wherein the cells form a part of a pathological tissue.

16. The system of claim 13, wherein the ionization threshold is from about $10^{10}$ Watts/cm$^2$ to about $10^{14}$ Watts/cm$^2$.

17. The system of claim 13, wherein a duration of said at least one optical pulse is selected so as to avoid heating of the cells by linear absorption.

18. An ablative procedure for destroying living cells present in a body of a subject, the cells being characterized by an ionization threshold, the ablative procedure comprising:
   administrating a plurality of particles to the body of the subject, at least a portion of each of said plurality of particles is made of a conducting material;
   directing at least one optical pulse toward at least a portion of the cells;
   said particles and said at least one optical pulse are selected and designed so as to provide a local enhancement of an optical field to a power per unit area which is beyond the ionization threshold of the cells, thereby destroying the cells via ionization.

19. The ablative procedure of claim 18, wherein said directing is by inserting a light transmitting device into the body of the subject.

20. The ablative procedure of claim 18, wherein each of said plurality of particles comprises an affinity component having affinity to the living cells.

21. The ablative procedure of claim 19, wherein said inserting said light transmitting device into the body is by endoscopy.

22. The ablative procedure of claim 19, wherein said inserting said light transmitting device into the body is by laparoscopy.

* * * * *